United States Patent
Cobbs

(10) Patent No.: US 6,497,609 B1
(45) Date of Patent: Dec. 24, 2002

(54) NIPPLE ENHANCER

(75) Inventor: Julia Cobbs, Edina, MN (US)

(73) Assignee: Bodyperks, Inc., Woodbury, MN (US)

( * ) Notice: Subject to any disclaimer, the term of this patent is extended or adjusted under 35 U.S.C. 154(b) by 0 days.

(21) Appl. No.: 09/952,687

(22) Filed: Sep. 12, 2001

Related U.S. Application Data

(60) Provisional application No. 60/232,730, filed on Sep. 15, 2000.

(51) Int. Cl.$^7$ ................................................. A41C 3/00
(52) U.S. Cl. ........................................... 450/57; 450/36
(58) Field of Search ........................ 450/36–38, 55–57, 450/58; 623/7.8; 2/267, 268

(56) References Cited

U.S. PATENT DOCUMENTS

| | | | |
|---|---|---|---|
| 2,391,417 A | * | 12/1945 | Hill ................................ 450/1 |
| 2,896,623 A | * | 7/1959 | Fitzgerald ..................... 450/57 |
| 3,976,083 A | * | 8/1976 | Schmidt ........................ 450/57 |
| 4,127,128 A | | 11/1978 | Schmidt |
| 4,195,639 A | * | 4/1980 | Lee ............................... 450/57 |
| 4,227,536 A | | 10/1980 | Shimenkov |
| 4,241,737 A | | 12/1980 | Schmidt |
| 4,640,288 A | * | 2/1987 | Hatori .......................... 450/57 |
| 4,778,465 A | | 10/1988 | Wilkins |
| 5,171,321 A | | 12/1992 | Davis |
| 5,782,672 A | * | 7/1998 | Woodley ....................... 450/57 |
| 5,824,075 A | * | 10/1998 | Thielbar ......................... 623/7 |
| 6,036,577 A | * | 3/2000 | Coburn ......................... 450/57 |
| 6,039,629 A | * | 3/2000 | Mitchell ....................... 450/57 |

OTHER PUBLICATIONS

"Natural Wear" by Camp 1997.

* cited by examiner

*Primary Examiner*—Gloria M. Hale
(74) *Attorney, Agent, or Firm*—Michael S. Sherrill

(57) ABSTRACT

A method of enhancing the tantalizing appearance of a covered female breast by placing a nipple enhancer between the breast and an article of clothing covering the breast in the absence of any adhesive so as to produce the appearance of an erect nipple through the article of clothing covering the breast.

8 Claims, 1 Drawing Sheet

NIPPLE ENHANCER

This application claims the benefit of United States Provisional Application No. 60/232,730, filed Sep. 15, 2000.

FIELD OF THE INVENTION

The invention relates to simulated nipples and nipple prosthesis.

BACKGROUND

Women occasionally seek to enhance their appearance and sensuousness, including an enhancement in the appearance of their breasts and/or nipples.

Wide varieties of surgically implantable prosthetic nipples are known. One example of a surgically implantable prosthetic nipple is described in U.S. Pat. No. 4,778,465 issued to Wilkins. While generally effective for enhancing the sensuousness of the breast and nipple, the use of such surgically implantable devices has declined significantly over the years due the expense of implanting the prosthetic nipples, the relative permanency of the enhancement, and the health risks associated with the implanting and removal of such breast implants.

One temporary method of enhancing the appearance and sensuousness of the female breasts and/or nipples is through the use of a nipple fashion bra comprised of a bra configured with an attachment mechanism for accommodating attachment of a simulated nipple. One example of such a nipple fashion bra is described in U.S. Pat. No. 3,976,083 issued to Schmidt. While significantly less expensive than surgically implanted prosthetic nipples and permitting a rapid return to the unenhanced appearance, such devices require the purchase and use of a specialty bra along with a supply of simulated nipples in order to achieve the desired appearance.

Externally positioned, temporary stand-alone prosthetic nipples are also known. U.S. Pat. No. 5,171,321 issued to Davis describes a prosthetic areola and nipple held in place over the natural areola and nipple of a female breast by an adhesive. While avoiding the drawbacks associated with implantable prosthetic nipples and nipple fashion bras, the stand-alone prosthetic nipples of Davis are cumbersome to use, uncomfortable to wear and difficult to remove due to the adhesive.

Accordingly, a need exists for a means by which a woman can simply, quickly, comfortably and inexpensively enhance the appearance and sensuousness of her breast and/or nipples while allowing a quick return to the unenhanced look and appearance of her breasts and/or nipples.

SUMMARY OF THE INVENTION

The invention is directed to a method of enhancing the tantalizing appearance of a covered female breast by producing the appearance of an erect nipple through the article of clothing covering the breast.

In a first embodiment, the method comprises the steps of (i) obtaining a pliable nipple enhancer wherein the nipple enhancer includes at least, (a) an areola portion having a convex outer surface and a concave inner surface configured and arranged to resemble the areola of a female breast, and (b) a nipple portion comprising a protuberance resembling the nipple of a female breast protruding from proximate the center of the outer surface of the areola portion of the nipple enhancer, (ii) donning an article of clothing, such as a bra, so as to cover at least a portion of at least one breast, and (iii) placing the nipple enhancer between the article of clothing and the breast with the inner surface of the areola portion of the nipple enhancer in direct physical contact with the breast in the absence of an adhesive. The nipple portion produces the appearance of an erect nipple through the article of clothing.

In a second embodiment, the method comprises the steps of (i) obtaining a pair of pliable nipple enhancers wherein each nipple enhancer includes at least, (a) an areola portion having a convex outer surface and a concave inner surface configured and arranged to resemble the areola of a female breast, and (b) a nipple portion comprising a protuberance resembling the nipple of a female breast protruding from proximate the center of the outer surface of the areola portion of the nipple enhancer, (ii) donning an article of clothing, such as a bra, so as to cover at least a portion of both breasts, and (iii) placing a first of the nipple enhancers between the article of clothing and a first breast and a second of the nipple enhancers between the article of clothing and a second breast with the inner surface of the areola portion of each nipple enhancer in direct physical contact with the breast in the absence of an adhesive. The nipple portion of each nipple enhancer produces the appearance of an erect nipple through the article of clothing.

In a third embodiment, the method comprises the steps of (i) donning an article of clothing which directly contacts the breast, such as a bra, and (ii) placing an adhesive free areola and nipple prosthesis between the article of clothing and the breast with the prosthesis in direct physical contact with the breast. At least the nipple portion of the prosthesis extends sufficiently from the outer contour of the breast to give the appearance of an erect nipple through the article of clothing.

DETAILED DESCRIPTION OF THE INVENTION INCLUDING A BEST MODE

Nomenclature

Figure 1:
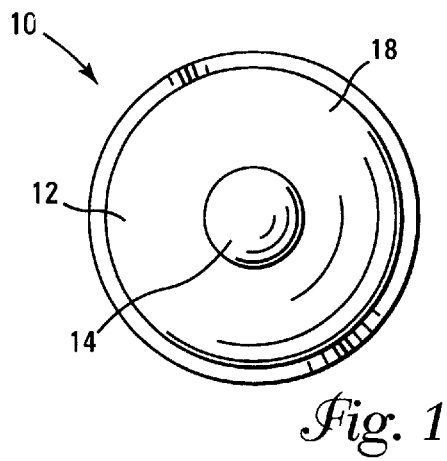
FIG. 1 is a front view of one embodiment of the nipple enhancer.
Figure 2:
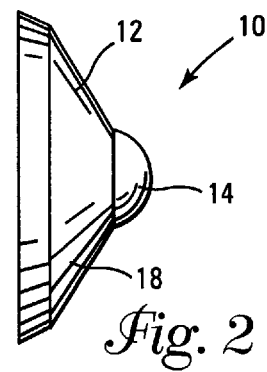
FIG. 2 is a side view of the nipple enhancer shown in FIG. 1.
Figure 3:
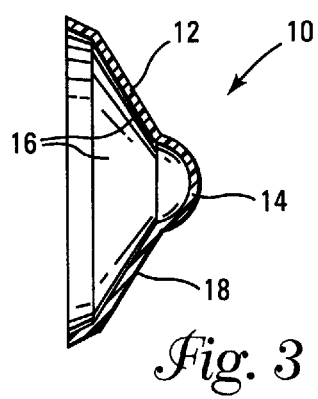
FIG. 3 is a cross-sectional side view of the nipple enhancer shown in FIG. 1.
Figure 4:
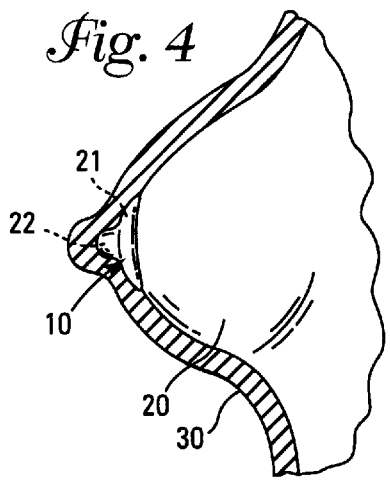
FIG. 4 is cross-sectional side view of the nipple enhancer of FIG. 1 placed between a female breast and an article of clothing.

10 Nipple Enhancer
12 Areola Portion of Nipple Enhancer
14 Nipple Portion of Nipple Enhancer
16 Inner Surface of Nipple Enhancer
18 Outer Surface of Nipple Enhancer
20 Breast
21 Areola of Breast
22 Nipple of Breast
30 Article of Clothing
40 Woman
50 Protrusion or Erect Nipple Construction The invention is directed to a method of enhancing the tantalizing appearance of a covered female breast 20 by placing a nipple enhancer 10 between the breast 20 and an article of clothing 30 covering the breast 20 so as to produce the appearance of an erect nipple 50 through the article of clothing 30 covering the breast 20.

The nipple enhancer 10 simulates the size, shape, and contour of a natural areola and nipple. The nipple enhancer 10 has a lower areola portion 12, generally shaped as a frustum of right cone, and an upper nipple portion 14, generally shaped as a spherical sector. The nipple portion 14 extends orthoganally from the top of the areola portion 12. The nipple enhancer 10 has a concave inner surface 16 and a convex outer surface 18.

The outer circumference of the areola portion 12 is preferably about two inches in diameter, with areola portions 12 of somewhat smaller or larger dimension contemplated by and within the scope of the invention. The nipple portion 14 preferably extends about 9/16 inches from the areola portion 12 and defines a width similar to the length, with nipple portions 14 of somewhat smaller or larger width or length and differing height:width ratios are also contemplated by and within the scope of the invention.

The nipple enhancer 10 is preferably made from silicone rubber due to its excellent biocompatibility, ease of manufacture and similarity in softness and texture to human tissue. Other materials such as polyvinylchloride, natural, and synthetic rubbers, polymers, polyurethane, polyethylene, and polypropylene will also work and are contemplated by and therefore within the scope of the invention. The nipple enhancer 10 can be pigmented to any desired color, but is preferably colored to one of the various shades of natural human areolas and nipples.

Use

Figure 5:
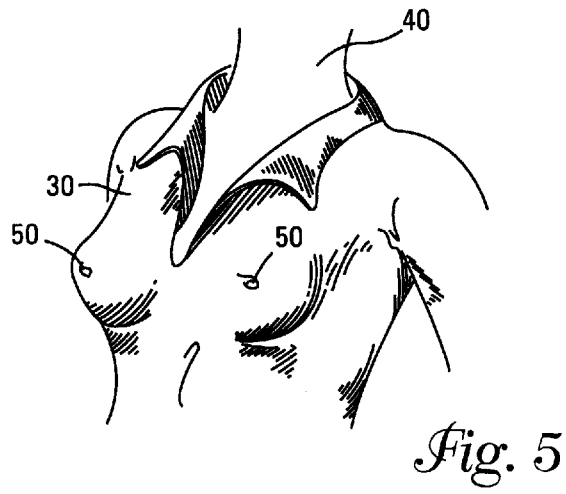
FIG. 5 is a front perspective view of a female torso wearing the nipple enhancers of FIG. 1.

The tantalizing appearance of a covered female breast 20 can be enhanced through use of the nipple enhancer 10 by simply (i) donning an article of clothing 30, such as a bra, so as to cover at least a portion of at least one breast 20, and (iii) placing the nipple enhancer 10 between the article of clothing 30 and the breast 20 with the inner surface 16 of the areola portion 12 of the nipple enhancer 10 in direct physical contact with the breast 20 in the absence of an adhesive. The nipple portion 14 thereby produces the appearance of an erect nipple 50 through the article of clothing 30, such as shown in FIG. 5.

The article of clothing 30 can be substantially any article of clothing 30 so long as the article of clothing 30 conforms closely to the shape of the breast 20. Exemplary article of clothing 30 include bras (not shown), stretchable tube tops (not shown), tight fitting halter tops (not shown), tight fitting t-shirts (not shown), bikini tops (not shown), one piece bathing suits (not shown), and dresses which conform to the bust line (not shown).

Following donning the article of clothing 30, the woman 40 stretches or removes a sufficient amount of the article of clothing 30 from over the breast 20 so as to allow access to the areola 21 and nipple 22 of the breast 20. The woman 40 then places the concave inner surface 16 of the nipple enhancer 10 over the areola 21 and nipple 22 of the breast 20, removes her hand from underneath the article of clothing 30 and allows the article of clothing 30 to return to its normal position so as to secure the nipple enhancer 10 in position over the areola 21 and nipple 22 of the breast 20. Alternatively, the nipple enhancer 10 can be positioned on the breast 20 at a location other than over the areola 21 and nipple 22 of the breast 20 to achieve a different appearance.

The outer contour of the article of clothing 30 conforms closely to the outer contour of the nipple enhancer 10. As shown in FIG. 5, the nipple portion 14 of the nipple enhancer 10 produces a prominent tantalizing protrusion 50 which simulates an erect nipple 22 and is highly visible from outside the clothing 30. It is possible for the wearer to wear more than one layer of clothing over the nipple enhancer 10 (e.g., wear a T-shirt over a brassiere) without a significant loss in the external appearance of an erect nipple 22.

An advantage of the method of the present invention is that the nipple enhancer 10 will remain in place for extended periods without the use of an adhesive.

Should the woman 40 desire to reposition the nipple enhancer 10, she need simply repeat the process used to initially place and position the nipple enhancer 10. The nipple enhancer 10 does not need to be removed from between the breast 20 and the article of clothing 30 to readjust positioning of the nipple enhancer 10. The adhesive free nature of the nipple enhancer 10 greatly simplifies repositioning of the nipple enhancer 10. As with initial placement and positioning of the nipple enhancer 10, the article of clothing 30 may simply be allowed to return to its original position following readjustment so as to secure the nipple enhancer 10 in position.

I claim:

1. A method of enhancing the tantalizing appearance of a covered female breast, comprising the steps of:
    (a) obtaining a pliable nipple enhancer, including at least;
        (i) an areola portion having a convex outer surface and a concave inner surface configured and arranged to resemble an areola of a female breast, and
        (ii) a nipple portion comprising a protuberance resembling a nipple of a female breast protruding from proximate the center of the outer surface of the areola portion of the nipple enhancer,
    (b) donning an article of clothing so as to cover and closely conform to at least a portion of at least one breast having a natural nipple; and
    (c) placing the nipple enhancers between the article of clothing and the breast with the inner surface of the areola portion of the nipple enhancer in direct physical contact with the breast in the absence of an adhesive;
    (d) whereby the nipple portion produces the appearance of an erect nipple through the article of clothing and is retained in position without adhesive.

2. The method of claim 1 wherein the article of clothing is a bra.

3. The method of claim 1 wherein the method further comprises positioning the nipple enhancer over the nipple of the breast.

4. A method of enhancing the tantalizing appearance of female breasts, comprising the steps of:
    (a) obtaining a pair of pliable nipple enhancers, wherein each nipple enhancer included at least;
        (i) an areola portion having a convex outer surface and a concave inner surface configured and arranged to resemble an areola of a female breast, and
        (ii) a nipple portion comprising a protuberance resembling a nipple of a female breast protruding from proximate the center of the outer surface of the areola portion of the nipple enhancer,
    (b) donning an article of clothing so as to cover and closely conform to at least a portion of both breasts; and
    (c) placing a first of the nipple enhancers between the article of clothing and a first breast having a natural nipple and a second of the nipple enhancers between the article of clothing and a second breast having a natural nipple with the inner surface of the areola portion of each nipple enhancer in direct physical contact with the breast in the absence of an adhesive;

(d) whereby the nipple portion of each nipple enhancer produces the appearance of an erect nipple through the article of clothing and is retained in position without adhesive.

5. The method of claim 4 wherein the article of clothing is a bra.

6. The method of claim 4 wherein the method further comprises positioning each nipple enhancer over the nipple of each breast.

7. A method of using an adhesive free areola and nipple prosthesis having an areola portion and a nipple portion, comprising the steps of:

(a) donning an article of clothing such that the clothing directly contacts and closely conforms to a breast having a natural nipple of a wearer; and (b) placing the adhesive free areola and nipple prosthesis between the article of clothing and the breast, such that the prosthesis is in direct physical contact with the breast;

(c) wherein (i) the breast defines an outer contour, (ii) the adhesive free areola and nipple prosthesis is retained in position without adhesive, and (iii) at least the nipple portion of the areola and nipple prosthesis extends sufficiently from the outer contour of the breast to give the appearance of an erect nipple through the article of clothing.

8. The method of claim 7 wherein the article of clothing is a bra.

* * * * *